(12) United States Patent
Otsubo

(10) Patent No.: US 12,137,939 B2
(45) Date of Patent: Nov. 12, 2024

(54) MEDICAL DEVICE AND TREATMENT METHOD

(71) Applicant: TERUMO KABUSHIKI KAISHA, Tokyo (JP)

(72) Inventor: Seiichi Otsubo, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 709 days.

(21) Appl. No.: 16/364,981

(22) Filed: Mar. 26, 2019

(65) Prior Publication Data

US 2019/0216503 A1    Jul. 18, 2019

Related U.S. Application Data

(63) Continuation of application No. PCT/JP2017/035214, filed on Sep. 28, 2017.

(30) Foreign Application Priority Data

Sep. 30, 2016    (JP) ................. 2016-193183

(51) Int. Cl.
*A61B 17/34* (2006.01)
*A61B 18/00* (2006.01)
(Continued)

(52) U.S. Cl.
CPC .......... *A61B 17/3476* (2013.01); *A61B 17/34* (2013.01); *A61B 17/3462* (2013.01);
(Continued)

(58) Field of Classification Search
CPC ............ A61B 18/1487; A61B 18/1497; A61B 18/1492; A61B 2018/00214;
(Continued)

(56) References Cited

U.S. PATENT DOCUMENTS 5,221,281 A    6/1993    Klicek
5,423,330 A  *  6/1995    Lee ................... A61B 10/0283
                                                   606/166
(Continued)

FOREIGN PATENT DOCUMENTS

CN    1706350 A    12/2005
CN    102860868 A   1/2013
(Continued)

OTHER PUBLICATIONS

Notification of the First Office Action issued by the National Intellectual Property Administration, PRC in corresponding Chinese Patent Application No. 2017800606189 on Dec. 22, 2020 (17 pages including partial English translation).
(Continued)

*Primary Examiner* — Eun Hwa Kim
(74) *Attorney, Agent, or Firm* — Buchanan Ingersoll & Rooney PC

(57) ABSTRACT

A medical device and a treatment method are disclosed which allow easy formation of a hole using energy and easy expansion of the formed hole without loss of tissue and allow an increase in working efficiency. A medical device is disclosed for forming a hole in a tissue in a living body and expanding the hole, the medical device including: a dilator having a first lumen formed inside and having a tip portion in which the first lumen opens on a distal side; and an output unit that outputs energy for denaturing the tissue and forming a hole, in which the output unit is disposed on a tip portion and formed discontinuously in the circumferential direction of the tip portion, and the outer diameter of the tip portion gradually decreases toward the distal side.

20 Claims, 12 Drawing Sheets

(51) Int. Cl.
*A61B 18/14* (2006.01)
*A61M 25/00* (2006.01)
*A61B 17/00* (2006.01)
*A61B 17/29* (2006.01)
*A61L 29/04* (2006.01)

(52) U.S. Cl.
CPC ......... *A61B 18/1487* (2013.01); *A61M 25/00* (2013.01); *A61B 17/00234* (2013.01); *A61B 2017/00867* (2013.01); *A61B 2017/2905* (2013.01); *A61B 2018/00827* (2013.01); *A61L 29/041* (2013.01)

(58) Field of Classification Search
CPC .. A61B 2018/1453; A61B 2018/00166; A61B 2018/00196; A61B 2018/00351; A61B 2018/0038; A61B 2018/00577; A61B 2018/142; A61B 2018/1253; A61B 17/3476; A61B 17/34; A61B 17/3462; A61B 17/00234; A61B 17/3417; A61B 18/1488
See application file for complete search history.

(56) References Cited

U.S. PATENT DOCUMENTS

| | | | |
|---|---|---|---|
| 5,423,848 | A | 6/1995 | Washizuka et al. |
| 6,302,898 | B1 | 10/2001 | Edwards et al. |
| 6,770,070 | B1 | 8/2004 | Balbierz |
| 7,397,016 | B2 | 7/2008 | Aoki et al. |
| 2002/0147447 | A1 | 10/2002 | Long |
| 2002/0169377 | A1* | 11/2002 | Khairkhahan . A61B 17/320725 600/433 |
| 2003/0130654 | A1 | 7/2003 | Kasahara et al. |
| 2005/0234436 | A1* | 10/2005 | Baxter ................... A61B 18/24 606/14 |
| 2005/0288747 | A1 | 12/2005 | Aoki et al. |
| 2009/0093810 | A1 | 4/2009 | Subramaniam et al. |
| 2009/0105654 | A1* | 4/2009 | Kurth ............. A61M 25/09041 604/170.03 |
| 2011/0224666 | A1* | 9/2011 | Davies ............... A61B 18/1492 606/41 |
| 2012/0239069 | A1* | 9/2012 | Benscoter .......... A61B 17/3478 606/185 |
| 2013/0281978 | A1 | 10/2013 | Nance et al. |
| 2013/0310833 | A1 | 11/2013 | Brown et al. |
| 2016/0175009 | A1* | 6/2016 | Davies ............... A61B 18/1492 606/191 |
| 2016/0262795 | A1* | 9/2016 | Urbanski .............. A61M 5/007 |
| 2016/0374721 | A1* | 12/2016 | Olomutzki ......... A61B 17/3205 606/129 |
| 2016/0374751 | A1* | 12/2016 | Davies ............... A61B 18/1477 606/48 |

FOREIGN PATENT DOCUMENTS

| | | |
|---|---|---|
| EP | 1 146 816 B1 | 10/2005 |
| EP | 2 077 807 A2 | 7/2009 |
| JP | H06142111 A | 5/1994 |
| JP | 2554849 B2 | 8/1996 |
| JP | 2000201946 A | 7/2000 |
| JP | 2012050538 A | 3/2012 |
| WO | 97/32532 A1 | 9/1997 |
| WO | 2008/045314 A2 | 4/2008 |
| WO | 2009/048824 A1 | 4/2009 |

OTHER PUBLICATIONS

International Search Report (with English translation) and Written Opinion issued in corresponding International Patent Application No. PCT/PCT/JP2017/035214, 6 pages (Dec. 5, 2017).
The extended European Search Report issued on Mar. 23, 2020, by the European Patent Office in corresponding European Patent Application No. 17856336.7-1115. (9 pages).
Office Action (Communication pursuant to Article 94(3) EPC) issued Aug. 30, 2022, by the European Patent Office in corresponding European Patent Application No. 17 856 336.7-1113. (5 pages).
Office Action (Decision to refuse a European Patent application and Annex to a communication) issued on Mar. 18, 2024, in corresponding European Patent Application No. 17856336.7. (13 pages).

* cited by examiner

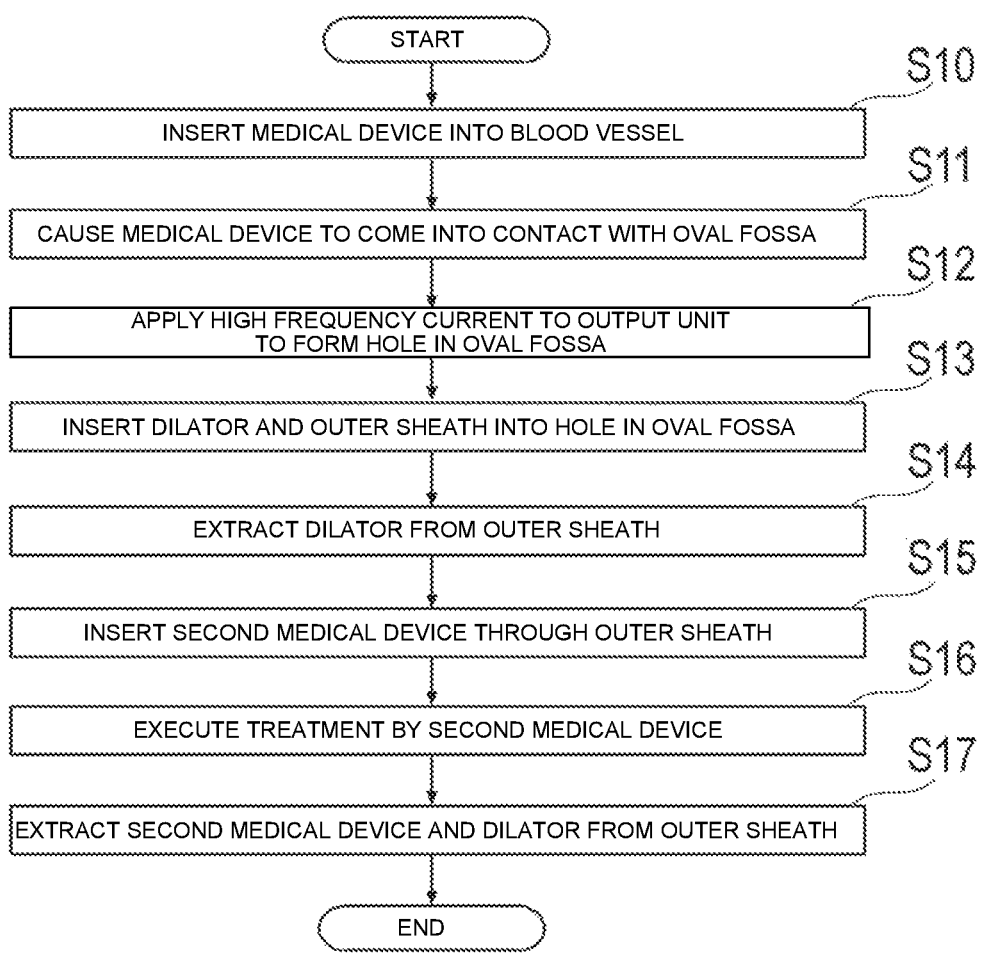

MEDICAL DEVICE AND TREATMENT METHOD

CROSS-REFERENCES TO RELATED APPLICATIONS

This application is a continuation of International Application No. PCT/JP2017/035214, filed on Sep. 28, 2017, which claims priority to Japanese Application No. 2016-193183, filed on Sep. 30, 2016, the entire content of both of which is incorporated herein by reference.

FIELD OF THE INVENTION

The present disclosure generally relates to a medical device and a treatment method for forming a hole in a tissue.

BACKGROUND DISCUSSION

A heart circulates blood by repeated contraction and expansion at suitable timing by a current flowing through a cardiac muscle tissue called a conducting system of the heart (i.e., cardiac conduction system). When the generation and the transmission of electric signals flowing through the conducting system of the heart become abnormal, the contraction and the expansion does not occur at the suitable timing causing an arrhythmia.

For the treatment for the arrhythmia, a method of interrupting the conduct path of signals that cause the arrhythmia by ablation in heating or cooling has been known. In order to perform this treatment method, an ablation device that is percutaneously inserted into a left atrium, and capable of performing ablation of a conduct path that is located at an opening of a pulmonary vein has been known. Such an ablation device is generally used because the ablation device is relatively minimally invasive and can obtain a relatively high effect.

In order to perform the ablation in the left atrium, a procedure called an atrial septum puncture (Brockenbrough method) in which a needle is inserted from the right atrium to a thin partition wall called a fossa ovalis (or oval fossa) in the atrial septum to create a hole that leads from the right atrium to the left atrium becomes necessary. The transseptal puncture needle (Transseptal Needle) is a device for performing the abovementioned atrial septum puncture that includes a mechanical puncture needle (Mechanical Needle) and a high frequency energy puncture needle (Radio Frequency Needle). The high frequency energy puncture needle forms a hole in the atrial septum by heating and denaturing a tissue with an electrode that outputs the high frequency energy. The high frequency energy puncture needle is inserted into a lumen of a dilator that is provided with the lumen penetrating through in the axial direction. After a hole is formed in the tissue with the high frequency energy puncture needle protruding from the dilator, the dilator is pushed down into the hole along the high frequency energy puncture needle to allow the hole to be widened. Thereafter, the high frequency energy is pulled out from the dilator to allow a guide wire to insert into the hole through the lumen of the dilator.

JP-A-2000-201946 describes a method of cutting a tissue with an electrode of a circular arc shape.

The puncture needle is used by being inserted into the lumen of the dilator, so that after the puncture is performed, the puncture needle needs to be pulled out from the dilator in order to insert the guide wire into the lumen of the dilator, which makes the operation troublesome. The device described in JP-A-2000-201946 does not include a function of making the formed hole relatively large, although the electrode does not need to be pulled out.

SUMMARY

A medical device and a treatment method are disclosed, which allow relatively easy formation of a hole using energy, relatively easy expansion of the formed hole, and an increase in working efficiency with maintained safety.

A medical device is disclosed for forming a hole in a tissue in a living body and expanding the hole, the medical device including: an elongated body having a lumen formed inside and having a tip portion in which the lumen opens on a distal side; and an output unit that outputs energy for denaturing the tissue and forming the hole, in which the output unit is disposed on the tip portion and formed discontinuously in a circumferential direction of the tip portion, and at least one of the tip portion and the output unit has an outer diameter gradually decreasing toward a distal side.

A treatment method is disclosed for forming a hole in a tissue in a living body and expanding the hole using the above medical device, the treatment method including: inserting a distal portion of the medical device into the living body; forming the hole by bringing the output unit into contact with the tissue and denaturing the tissue; and moving the elongated body to the distal side to widen the hole in the tissue by at least one of the tip portion and the output unit.

In the medical device and the treatment method configured as the above, the output unit discontinuous in the circumferential direction of the tip portion is provided to hollow out the tissue and help prevent the tissue from falling off, so that it is possible to retain the safety and form a hole using the energy. In addition, the outer diameter of at least one of the tip portion and output unit gradually decreases toward the distal side, so that it is possible to rather easily expand the hole by pushing down the tip portion or the output unit into the hole formed in the tissue. In addition, the output unit is not disposed in the lumen of the elongated body, so that it is possible to cause the guide wire to reach a portion ahead of the hole through the lumen that opens in the tip portion, without pulling out the output unit to the outside of the living body, which helps prevent the output unit from being pulled out to the outside of the living body, so that it is possible to enhance the working efficiency.

In accordance with an aspect, a medical device is disclosed for forming a hole in a tissue in a living body and expanding the hole, the medical device comprising: an elongated body having a lumen formed inside of the elongated body and having a tip portion in which the lumen opens on a distal side; and an output unit that outputs energy for denaturing the tissue and forming the hole, the output unit being disposed on the tip portion of the elongated body and formed discontinuously in a circumferential direction of the tip portion, and at least one of the tip portion and the output unit has an outer diameter decreasing toward a distal side of the medical device.

In accordance with another aspect, a medical device for forming a hole in a tissue in a living body and expanding the hole, the medical device comprising: an elongated body having a lumen formed inside of the elongated body and having a tip portion in which the lumen opens on a distal side; an output unit that outputs energy for denaturing the tissue and forming the hole, the output unit being disposed on the tip portion of the elongated body and formed discontinuously in a circumferential direction of the tip portion, and the tip portion and the output unit each having an outer diameter decreasing toward a distal side of the medical device.

In accordance with an aspect, a method is disclosed for forming a hole in a tissue in a living body and expanding the hole, the method comprising: inserting a guidewire into the living body; inserting an elongated body having a lumen formed inside the elongated lumen, the elongated body having a tip portion in which the lumen opens on a distal side and having an energy portion on a distal end portion of the tip portion along the guide wire into the living body; penetrating an atrial septum between a right atrium and a left atrium of a heart to create an opening in the atrial septum with the energy portion without a needle; increasing the opening to a larger size with the tip portion; and moving the guidewire through the lumen of the tip portion to the left atrium

BRIEF DESCRIPTION OF THE DRAWINGS

FIGS. 6A to 6C are cross-sectional views illustrating states where a puncture is performed by the medical device according to the embodiment, wherein FIG. 6A illustrates the state where the medical device penetrates through a hole of an fossa ovalis; FIG. 6B illustrates the state where the medical device is located; and FIG. 6C illustrates the state where the fossa ovalis punctured by the medical device.

FIGS. 8A to 8C are cross-sectional views illustrating states where the puncture is performed by the medical device, wherein FIG. 8A illustrates the state where the medical device is inserted into a right atrium; FIG. 8B illustrates the state where a guide wire is inserted into a left atrium; and FIG. 8C illustrates the state where the dilator is pulled out from the outer sheath.

FIG. 9 is a flowchart for explaining a procedure using the medical device.

FIGS. 11A and 11B are transverse cross-sectional views illustrating denaturation examples of the medical device, wherein FIG. 11A illustrates a first denaturation example; and FIG. 11B illustrates a second denaturation example.

FIGS. 12A and 12B are views illustrating a third denaturation example of the medical device, wherein FIG. 12A is a vertical cross-sectional view; and FIG. 12B is a transverse cross-sectional view along the XIIB-XIIB line in FIG. 12A.

FIGS. 13A and 13B are transverse cross-sectional views illustrating denaturation examples of the medical device, wherein FIG. 13A illustrates a fourth denaturation example; and FIG. 13B illustrates a fifth denaturation example.

FIGS. 14A and 14B are views illustrating a sixth denaturation example of the medical device, wherein FIG. 14A is a vertical cross-sectional view; and FIG. 14B is a transverse cross-sectional view along the XIVB-XIVB line in FIG. 14A.

FIGS. 15A and 15B are cross-sectional views illustrating denaturation examples of the medical device, wherein FIG. 15A illustrates a seventh denaturation example; and FIG. 15B illustrates an eighth denaturation example.

DETAILED DESCRIPTION

Figure 1:
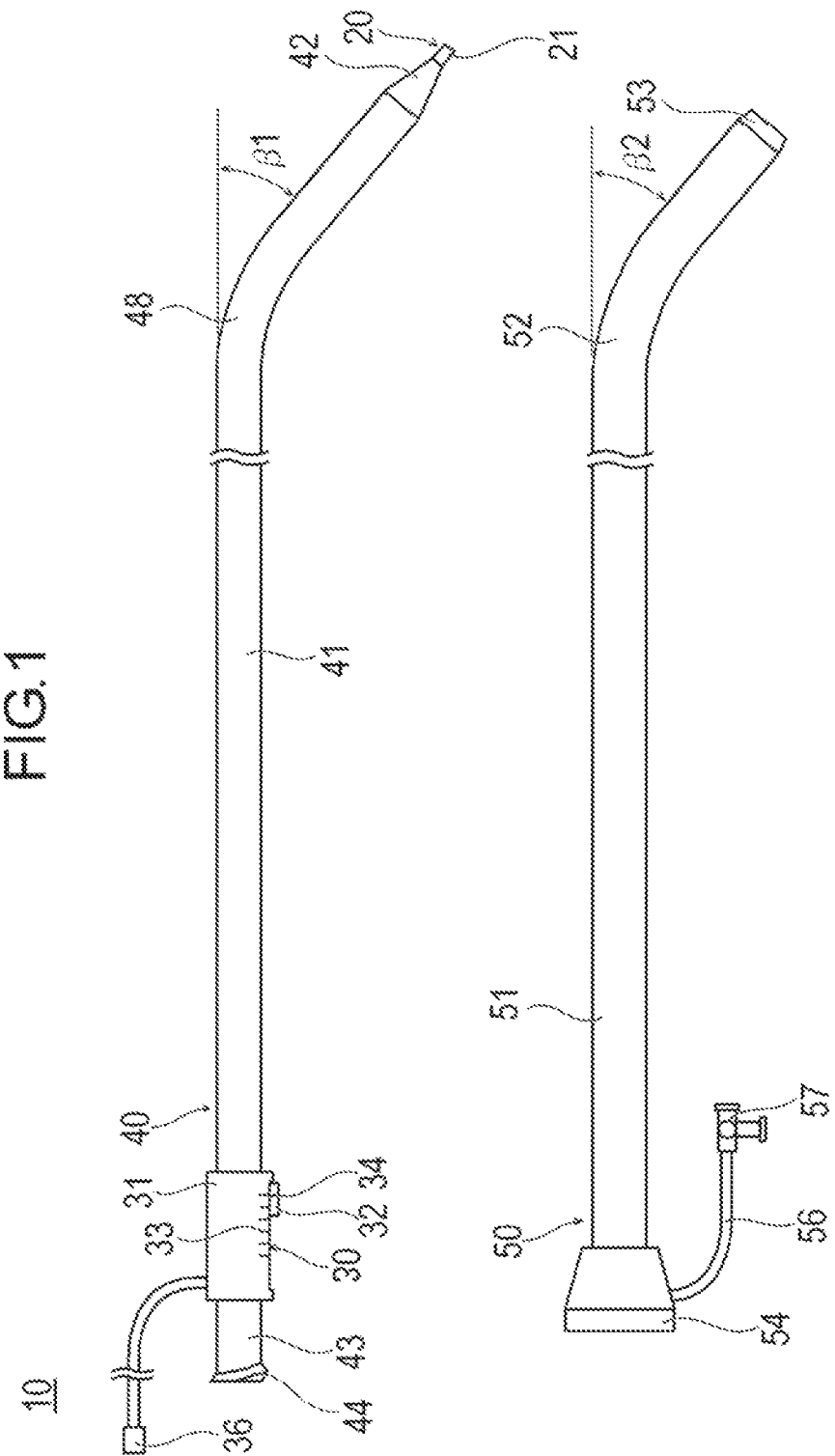
FIG. 1 is a plan view illustrating a medical device according to an embodiment.
Figure 2:
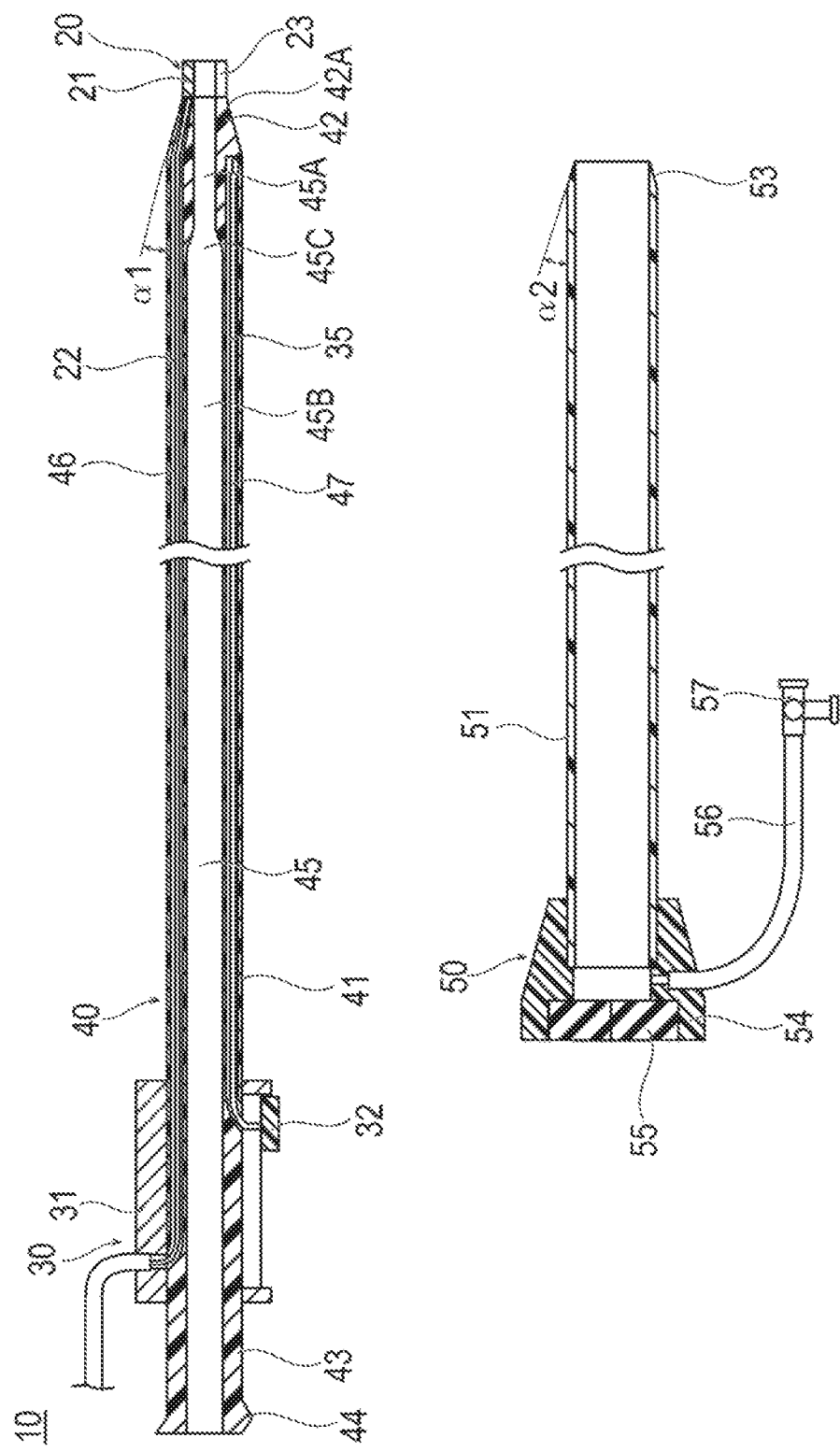
FIG. 2 is a cross-sectional view illustrating a dilator and an outer sheath.
Figure 3:
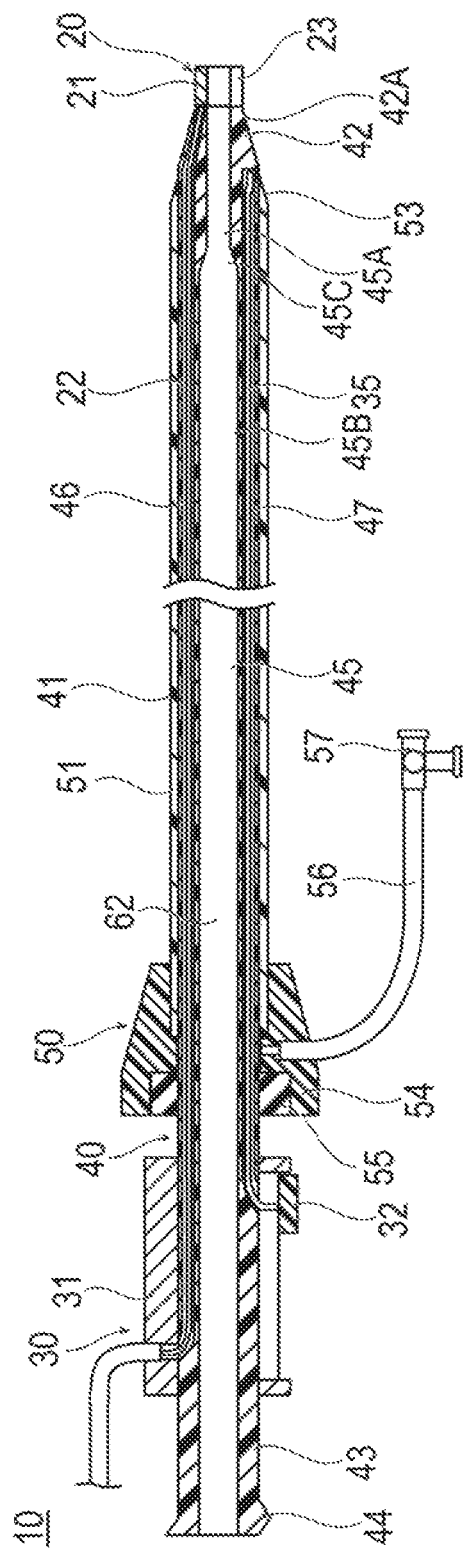
FIG. 3 is a cross-sectional view illustrating the medical device according to the embodiment.
Figure 4:
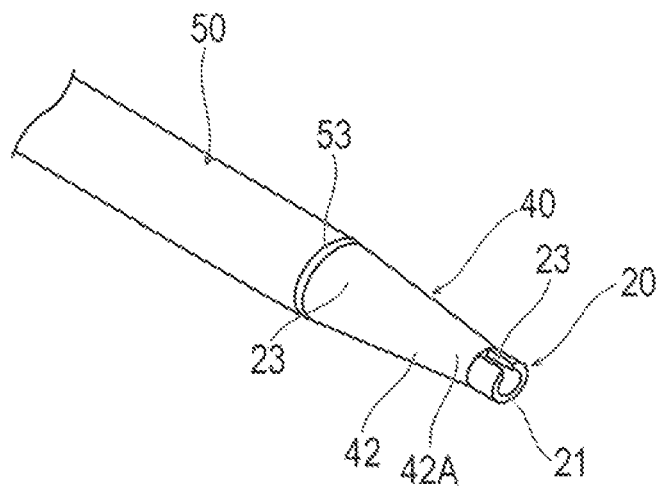
FIG. 4 is a perspective view illustrating a distal portion of the medical device according to the embodiment.

Hereinafter, an embodiment according to the present disclosure will be described with reference to the drawings. Note that, the size ratios in the drawings may be exaggerated for convenience of explanation, and may be different from the actual ratios in some cases. In the present description, a side of the device to be inserted into a blood vessel is referred to as a "distal side", and a hand-side where the device is operated is referred to as a "proximal side".

Figure 5:
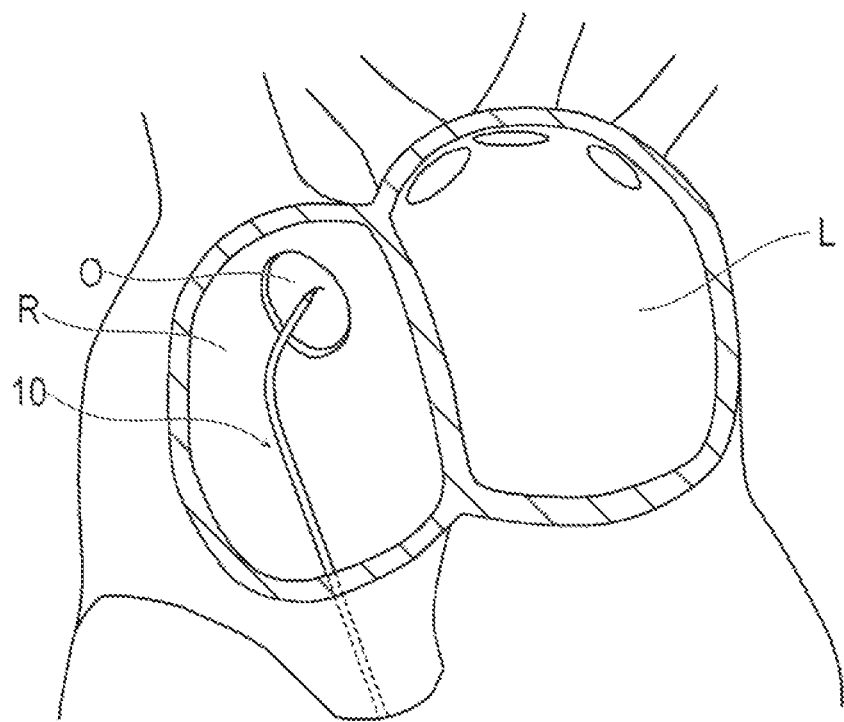
FIG. 5 is a partial cross-sectional view illustrating an interior of a heart.

A medical device 10 according to the embodiment of the present disclosure can be used for forming a hole in an fossa ovalis O in an atrial septum from a right atrium R, and providing an access route that leads from the right atrium R to a left atrium L (see FIG. 5). When there is an access route in the fossa ovalis O, a plurality of treatment devices having been percutaneously inserted into the large vein is guided to the right atrium R, and then can be rather easily inserted into the left atrium. Examples of the treatment devices include an ablation catheter, a ring catheter, and the like.

The medical device 10 according to the embodiment includes, as illustrated in FIGS. 1 to 4, a dilator 40 (elongated body), an energy output unit 20, an operation unit 30, and an outer sheath 50.

In accordance with an exemplary embodiment, the dilator 40 can be used for widening a hole in the fossa ovalis O that is formed by the energy output unit 20. The dilator 40 includes a dilator center portion 41 having an approximately constant outer diameter, a tip portion 42 located distal from (i.e., distally of) the dilator center portion 41, and a dilator proximal portion 43 located proximal from (i.e., proximally of) the dilator center portion 41. In accordance with an exemplary embodiment, the dilator center portion 41 can be a pipe body (or tubular body) having an approximately constant outer diameter. The tip portion 42 has an outer diameter decreasing, for example, in a tapered shape. An inclined angle α1 of an outer peripheral surface of the tip portion 42 relative to the central axis is set as appropriate, and can be, for example, 1 degree to 80 degrees, more preferably 1 degree to 30 degrees, and still more preferably 1 degree to 10 degrees. The dilator proximal portion 43 having a luer taper shape includes a male connector 44 capable of interlocking with a lock-equipped connector, on an outer peripheral surface of the male connector 44.

In accordance with an exemplary embodiment, the dilator 40 includes a first lumen 45 (lumen), a second lumen 46, and a third lumen 47 being formed in the dilator 40. The first lumen 45 is located at a central portion of the dilator 40 in a cross-section vertical to a central axis of the dilator 40. The first lumen 45 penetrates through the dilator 40 in the axial direction. The first lumen 45 opens in an end portion of the tip portion 42 on the distal side where an outer diameter of the tip portion 42 is reduced to minimum. The first lumen 45 is capable of a receiving a guide wire (not shown). The second lumen 46 is configured to receive a conductive wire 22 of the energy output unit 20. The second lumen 46 opens in an end portion of the dilator 40 on the distal side, and opens in the vicinity of the operation unit 30 of the dilator 40. The third lumen 47 is configured to receive an operation wire 35 for bending the dilator 40. The third lumen 47 opens in the vicinity of the operation unit 30 of the dilator 40, and extends to a distal portion of the dilator 40. The third lumen 47 may externally open in the distal portion of the dilator 40 or may not open into the distal portion of the dilator 40.

The first lumen 45 is provided with a distal side lumen 45A on the distal side, a proximal side lumen 45B having an inner diameter larger than that of the distal side lumen 45A, a central lumen 45C having an inner diameter that changes between the distal side lumen 45A and the proximal side lumen 45B. In accordance with an exemplary embodiment, the inner diameter of the proximal side lumen 45B is larger than the outer diameter of the guide wire to be inserted, which helps enable the guide wire inserted into the proximal side lumen 45B to move rather smoothly along an inner peripheral surface of the dilator 40. In accordance with an exemplary embodiment, the central lumen 45C smoothly guides the guide wire passing through the proximal side lumen 45B to the distal side lumen 45A. The inner diameter of the distal side lumen 45A is an inner diameter that allows the guide wire to slide while coming into contact with the distal side lumen 45A with a relatively small clearance, which helps reduce the outer diameter of the dilator 40 at the end portion on the distal side, so that the dilator 40 can smoothly enter a hole in a tissue.

In accordance with an exemplary embodiment, the dilator 40 includes a dilator bend 48 (bend) that bends at a prescribed angle in a state where no external force acts, in the distal portion of the dilator 40. The dilator bend 48 plays a role in causing the distal portion of the dilator 40 to be directed toward the fossa ovalis O. A direction that the dilator bend 48 bends toward the distal side is equivalent to a direction that the third lumen 47 is provided with respect to the central axis of the dilator 40.

In accordance with an exemplary embodiment, a length of the dilator 40 in the axial direction is set as appropriate, and can be, for example, 500 mm to 800 mm. The outer diameter of the dilator 40 is set as appropriate, and can be, for example, 1.0 mm to 10.0 mm. The inner diameter of the distal side lumen 45A is set as appropriate, and can be, for example, 0.3 mm to 5.0 mm. The inner diameter of the second lumen 46 is set as appropriate in accordance with the outer diameter of the conductive wire 22 to be received, and can be, for example, 0.1 mm to 2.0 mm. The inner diameter of the third lumen 47 is set as appropriate in accordance with the outer diameter of the operation wire 35 to be received, and can be, for example, 0.1 mm to 2.0 mm. An angle β31 of the dilator bend 48 relative to a proximal portion of the dilator 40 is not specially limited, and can be, for example, 10 degrees to 90 degrees, more preferably 30 degrees to 80 degrees, and still more preferably 40 degrees to 70 degrees. The length from a distal side end portion of the dilator 40 to the dilator bend 48 is set as appropriate, and can be, for example, 10 mm to 150 mm, more preferably 15 mm to 90 mm, and still more preferably 20 mm to 70 mm.

The dilator 40 material preferably has flexibility, and for example, the material of the dilator 40 can be a polyolefin such as polyethylene or polypropylene, polyamide, polyester such as polyethylene terephthalate, fluorinated polymers such as polytetrafluoroethylene (PTFE), tetrafluoroethylene ethylene copolymer (ETFE), polyether ether ketone (PEEK), polyimide, shape memory alloys, metal such as stainless steel, tantalum, titanium, platinum, gold, and tungsten, and the like can be used suitably. In addition, the dilator 40 may include a material having good visibility for an X-ray contrast material or ultrasound.

In accordance with an exemplary embodiment, the energy output unit 20 is configured to output energy for creating a hole in the fossa ovalis O. The energy output unit 20 includes an output unit 21 that is an electrode disposed in the distal portion of the dilator 40, and the conductive wire 22 that is connected to the output unit 21 and conducts the current to output unit 21. In accordance with an exemplary embodiment, a counter electrode that is an electrode to be paired up with the output unit 21 is attached to a body surface. The conductive wire 22 penetrates through the second lumen 46. An end portion of the conductive wire 22 on the distal side is connected to the output unit 21. An end portion of the conductive wire 22 on the proximal side is derived from the second lumen 46 in the proximal portion of the dilator 40, and is connected to a connector 36 of the operation unit 30. In accordance with an exemplary embodiment, the connector 36 is capable of being connected to an external power supply device that supplies a high frequency current to the energy output unit 20. In accordance with an exemplary embodiment, the conductive wire 22 may be disposed along an outer surface of the dilator 40 without being disposed in the second lumen 46. In this case, a groove that allows the conductive wire 22 to be disposed is preferably formed in the outer surface of the dilator 40. In addition, a surface of the conductive wire 22 is coated with an insulator. The output unit 21 in which the high frequency current flows through the conductive wire 22 heats and denatures a tissue, thereby forming a hole. The output unit 21 is provided on the distal side end portion of the tip portion 42. The output unit 21 is joined to (engaged in) the tip portion 42 of the dilator 40 by bonding or the like. In accordance with an exemplary embodiment, the output unit 21 has an approximately cylindrical shape with the central axis the same as the central axis of the dilator 40, and includes a lumen that penetrates in the axial direction. The lumen of the output unit 21 communicates with the distal side lumen 45A. The output unit 21 includes a slit 23 that is formed in a portion in the circumferential direction. The slit 23 is a cut that extends from the distal side end of the output unit 21 to the proximal side end of the output unit 21, and penetrates from the outer surface of the output unit 21 to the inner surface of the output unit 21. Accordingly, the shape of the output unit 21 in a cross-section vertical to the central axis of the dilator 40 is a C-character shape. Therefore, the output unit 21 has a concave shape on a side toward the central axis of the first lumen 45 as viewed from the distal side. The output unit 21 is provided in a range of less than 360 degrees in a direction that surrounds the central axis of the dilator 40. The inner diameter of an inner peripheral surface of the output unit 21 is equivalent to the inner diameter of the distal side lumen 45A, which helps enables the guide wire to be smoothly passed through from the distal side lumen 45A to the output unit 21. In accordance with an exemplary embodiment, the inner diameter of the output unit 21 need not to be equivalent to the inner diameter of the distal side lumen 45A. The outer diameter of an outer peripheral surface of the output unit 21 is smaller than the maximum outer diameter of the tip portion 42 (the outer diameter of the dilator center portion 41), which helps prevent a hole in the fossa ovalis O being formed by the output unit 21 from being too large, and the tapered tip portion 42 can expand the hole in the fossa ovalis O. When a hole to be formed in the fossa ovalis O is too large, the hole remains after the procedure has completed, and blood passes through the hole and circulates between the right atrium R and the left atrium L. Therefore, the outer diameter of the output unit 21 is preferably not too large. Moreover, when a hole to be formed in the fossa ovalis O is too small, a resistance becomes relatively large when the tip portion 42 expands the hole, which makes the procedure difficult. Therefore, the outer diameter of the output unit 21 is preferably not too small. The direction that the slit 23 (notch) is provided is equivalent to the direction that the third lumen 47 is provided with respect to the central axis of the dilator 40.

A length of the output unit 21 in the axial direction is set as appropriate, and can be, for example, 0.1 mm to 5.0 mm, preferably 0.1 mm to 3.0 mm, and more preferably 0.1 mm to 1.5 mm. The angle at which the output unit 21 surrounds the central axis of the first lumen 45 is set as appropriate, and can be, for example, 1 degree to 270 degrees, and preferably 45 degrees to 180 degrees. The outer diameter of the output unit 21 is set as appropriate, and can be, for example, 0.5 mm to 5.0 mm, preferably 0.5 mm to 4.0 mm, and more preferably 1.0 mm to 2.0 mm. The inner diameter of the output unit 21 is set as appropriate, and can be, for example, 0.3 mm to 4.5 mm, preferably 0.3 mm to 3.5 mm, and more preferably 0.5 mm to 1.5 mm. In accordance with an exemplary embodiment, the output unit 21 of the energy output unit 20 need not use the high frequency current, but may use, for example, energy such as electromagnetic waves, laser, or cooling, as long as it can denature the tissue to form a hole.

The material of the output unit 21 is not specially limited as long as it has the conductivity, and can be, for example, stainless steel, Au (gold), Pt (platinum), tungsten, or titanium.

In accordance with an exemplary embodiment, the operation unit 30 includes a casing 31 that is fixed to the proximal portion of the dilator 40, a slide part 32, the operation wire 35, and the connector 36. The slide part 32 is disposed to the casing 31 so as to be slidable along the axial direction of the dilator 40. The operation wire 35 is stored in the third lumen 47 of the dilator 40. An end portion of the operation wire 35 on the proximal side is fixed to the slide part 32. An end portion of the operation wire 35 on the distal side is fixed to the distal portion of the dilator 40 in the interior of the third lumen 47. In accordance with an exemplary embodiment, the end portion of the operation wire 35 on the distal side may be fixed to the dilator 40 at a position where being derived from the third lumen 47, not in the interior of the third lumen 47. In addition, the operation wire 35 may be fixed to any portion in a distal portion of the energy output unit 20 (for example, the output unit 20), not to the dilator 40. The direction that the third lumen 47 is provided with respect to the central axis of the dilator 40 is equivalent to the direction that the dilator bend 48 bends toward the distal side. Therefore, when the slide part 32 is moved toward the proximal side with respect to the casing 31, the operation wire 35 that is fixed to the slide part 32 also moves toward the proximal side in the third lumen 47. With this, a contractive force acts on the side on which the third lumen 47 is provided with respect to the central axis of the dilator 40. Therefore, the dilator bend 48 can be bent so as to obtain a relatively large bending angle β1. In addition, when the slide part 32 is returned to the distal side with respect to the casing 31, the operation wire 35 moves toward the distal side in the third lumen 47, which decreases the contractive force that act on the dilator 40. Therefore, the dilator bend 48 can be returned to an original shape. The bending angle β1 of the dilator bend 48 is changed to allow the dilator 40 to be directed in a suitable direction.

As illustrated in FIG. 1, a first display part 33 such as a scale is provided on an outer surface of the casing 31 along the movable range of the slide part 32. In addition, a second display part 34 to be paired with the first display part 33 is provided on an outer surface of the slide part 32, which helps enable a position of the slide part 32 relative to the casing 31 to be rather easily grasped. Therefore, the bending angle β1 of the dilator bend 48 can be grasped from the position of the slide part 32 relative to the casing 31. In accordance with an exemplary embodiment, the first display part 33 and the second display part 34 that are respectively provided to the casing 31 and the slide part 32 are not necessarily scales (i.e., a series of marks or points at known intervals), but may be, for example, signs, figures, or characters. Moreover, the first display part 33 may be provided to an outer peripheral surface of the dilator 40, not to the casing 31.

The end portion of the conductive wire 22 on the proximal side to be derived from the second lumen 46 is connected to the connector 36. The connector 36 is capable of being connected to the external power supply device that supplies the high frequency current to the energy output unit 20.

In accordance with an exemplary embodiment, the outer sheath 50 provides an access route of a treatment device such as an ablation catheter. The outer sheath 50 includes a sheath main body 51, a hub 54 that is interlocked with a proximal portion of the sheath main body 51, a port part 56 that communicates with the hub 54, and a valve body 55 in the interior of the hub 54.

The sheath main body 51 is an elongated pipe body that stores in the sheath main body 51, the dilator 40 so as to be movable in the axial direction. The sheath main body 51 has an inner peripheral surface that allows the dilator 40 to smoothly slide with the sheath main body 51. The sheath main body 51 includes a sheath bend 52 that bends at a prescribed angle in a natural state, in a distal portion of the sheath main body 51. An angle β2 of the sheath bend 52 relative to the proximal portion of the sheath main body 51 is not specially limited, and can be, for example, 0 degrees to 90 degrees, more preferably 20 degrees to 70 degrees, and still more preferably 40 degrees to 60 degrees. The sheath bend 52 plays a role in causing the output unit 21 that is disposed to the dilator 40 having been inserted into the right atrium R to direct toward the fossa ovalis O.

In accordance with an exemplary embodiment, the sheath main body 51 includes a sheath tapered portion 53 a diameter of which is reduced toward the distal side in a tapered shape, in the distal side end portion. A lumen of the sheath main body 51 is opened in the end portion of the sheath tapered portion 53 where the diameter is reduced to minimum. An inclined angle α2 relative to the central axis of the sheath tapered portion 53 is set as appropriate, and can be, for example, 1 degrees to 15 degrees, more preferably 2 degrees to 10 degrees, and still more preferably 3 degrees to 7 degrees. In a state where the outer sheath 50 is inserted into the dilator 40, the sheath tapered portion 53 can be located proximal from the tip portion 42 of the dilator 40, and can be located to be continuous with the tip portion 42. An inner peripheral surface of the sheath main body 51 preferably has a clearance with the outer peripheral surface of the dilator 40 so as to allow the outer peripheral surface of the dilator 40 to slidably come into contact with the sheath main body 51.

The sheath main body 51 allows the dilator 40 to penetrate through the sheath main body 51 over a total length of the sheath main body 51. Accordingly, the length of the sheath main body 51 in the axial direction is shorter than that of the dilator 40. A length of the sheath main body 51 in the axial direction is set as appropriate, and can be, for example, 400 mm to 790 mm. The outer diameter of the sheath main body 51 is set as appropriate, and can be, for example, 1.1 mm to 11.0 mm. The inner diameter of the sheath main body 51 is set as appropriate, and can be, for example, 1.05 mm to 10.95 mm. A radial clearance between the inner peripheral surface of the sheath main body 51 and the outer peripheral surface of the dilator 40 is set as appropriate, and can be, for example, 0.01 mm to 1.00 mm.

The material of the sheath main body 51 is preferably a material having flexibility, and for example, the sheath main body 51 material can be a polyolefin such as polyethylene or polypropylene, polyamide, polyester such as polyethylene terephthalate, fluorinated polymers such as polytetrafluoroethylene (PTFE), tetrafluoroethylene ethylene copolymer (ETFE), polyether ether ketone (PEEK), polyimide, and the like.

The hub 54 is provided in the proximal portion of the sheath main body 51, and communicates with the lumen of the sheath main body 51. The dilator 40 penetrates through the hub 54. The port part 56 is interlocked with the hub 54, and communicates with the lumen of the sheath main body 51 through a lumen of the hub 54. The port part 56 includes a three-way stopcock 57 in an end portion of the port part 56. In accordance with an exemplary embodiment, a syringe or the like can be connected to the three-way stopcock 57 to allow priming to be performed in the lumen of the sheath main body 51, and a contrast agent, a drug, or the like to be injected into the sheath main body 51.

The valve body 55 is a member for sealing the hub 54 and the lumen of the sheath main body 51. The valve body 55 is flexibly deformable, and is disposed to an inner peripheral surface of the hub 54. The valve body 55 slidably comes into contact with the outer peripheral surface of the dilator 40. Moreover, in a state where the dilator 40 is inserted, the valve body 55 can press against the dilator 40 by an elastic force, and fix the dilator 40 and the outer sheath 50 to each other. Note that, even when the dilator 40 and the outer sheath 50 are fixed by the valve body 55, the dilator 40 and the outer sheath 50 can be relatively moved in the axial direction in such a manner that the dilator 40 and the outer sheath 50 are gripped, and a force is applied to the dilator 40 and the outer sheath 50. In accordance with an exemplary embodiment, the dilator 40 is pulled out from the hub 54 to close a hole portion of the valve body 55 into which the dilator 40 is inserted, and seal the lumen of the hub 54 from the proximal side. The valve body 55 is a member in which a cut is made in the center of a disk-like elastic body, for example. Examples of the elastic body include natural rubber, silicone rubber, and various kinds of elastomer. The valve body 55 suppresses blood from leaking through the outer sheath 50, and suppresses the air from mixing into the body, while allowing the insertion and the extraction of the dilator 40.

In a state where the dilator 40 and the outer sheath 50 are combined, positions, bending directions, and bending angles of the dilator bend 48 and the sheath bend 52 preferably coincide or substantially coincide with each other, which helps enable the output unit 21 to direct in a desired direction.

Next, using the medical device 10 according to the embodiment, a method of creating a hole in the fossa ovalis O, and providing an access route for a device such as an ablation catheter will be described with reference to a flowchart of FIG. 9.

Figure 6A:
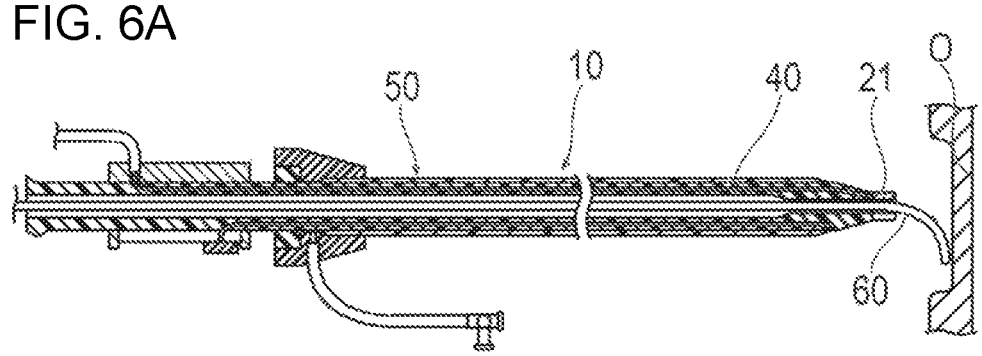

Firstly, a needle is punctured into a femoral vein, and a short guide wire is inserted into this needle. Next, the needle is extracted, and a catheter introducer is inserted into a blood vessel along the short guide wire. Next, the medical device 10 in which the dilator 40 is inserted into the interior of the outer sheath 50 is prepared (see FIG. 3). Subsequently, the short guide wire is extracted, and a guide wire 60 is inserted into the catheter introducer. Next, the catheter introducer is extracted while the guide wire 60 is left in the blood vessel, a proximal side end portion of the guide wire 60 is inserted into the lumen 45 from the distal side end portion of the dilator 40, and the medical device 10 is inserted into the blood vessel (Step S10). Subsequently, while causing the guide wire 60 to proceed, a distal portion of the medical device 10 is gradually pushed ahead to the right atrium R. Next, the medical device 10 is temporarily inserted along the guide wire 60 from the right atrium R into the large vein. Subsequently, when the medical device 10 is backed and is led into the right atrium R, as illustrated in FIG. 5 and FIG. 6A, the distal side end portion of the dilator 40 is automatically guided to the vicinity of the fossa ovalis O. Thereafter, while an X-ray image is checked, a distal side end portion of the guide wire 60 is led into the interior of the dilator 40. In accordance with an exemplary embodiment, the guide wire 60 may be temporarily extracted from the dilator 40.

Figure 6B:
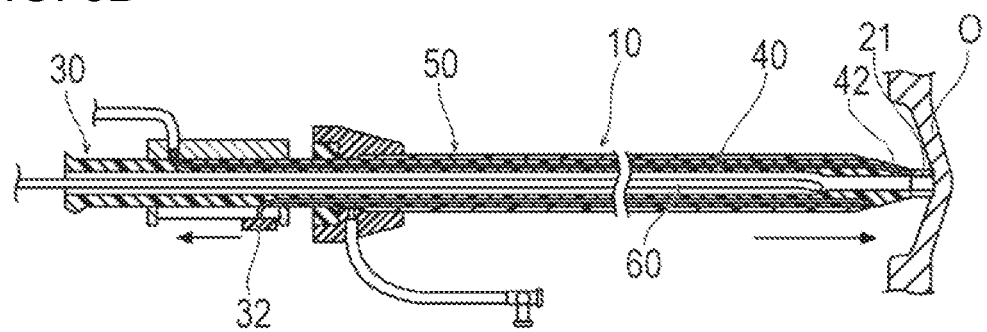

Next, while the interiors of the left atrium L and the right atrium R being observed with an intra cardiac echo catheter (ICE), the medical device 10 is pushed down to the distal side. With this, as illustrated in FIG. 6B, the fossa ovalis O is pushed to the side of the left atrium L by the output unit 21, and becomes a protruded state (Step S11). In this process, the distal portions of the outer sheath 50 and the dilator 40 are being bent, so that the end portion of the dilator 40 on the distal side easily directs to the fossa ovalis O. Moreover, when an orientation of the dilator 40 is undesirable, the slide part is moved with respect to the casing 31 to allow the angle β1 of the dilator bend to be changed, which can help adjust the dilator 40 to the desired direction. Note that, the fossa ovalis O need not to protrude to the side of the left atrium L. In the output unit 21, a side opposite to a side where the slit 23 is provided is located on an upper edge portion side of the fossa ovalis O.

Figure 6C:
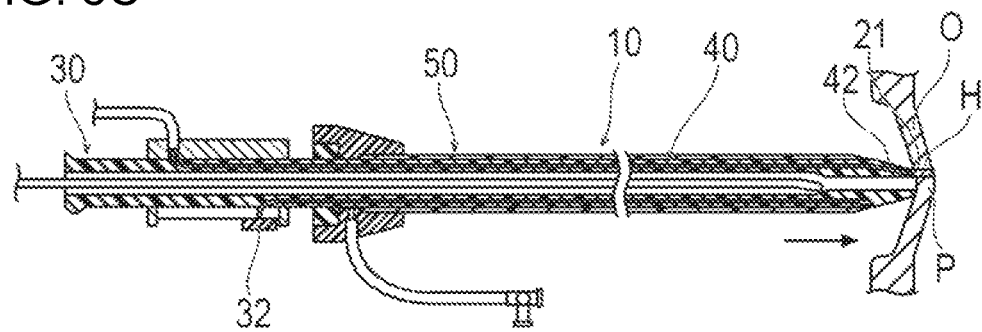
Figure 7:
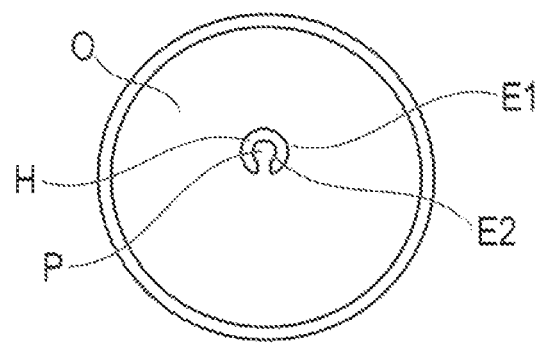
FIG. 7 is a plan view illustrating the hole in the fossa ovalis formed by the medical device.

Next, the medical device 10 is pushed down while a high frequency current is applied to the output unit 21. With this, as illustrated in FIG. 6C and FIG. 7, a tissue that is in contact with the output unit 21 is cauterized, a hole H in accordance with the C-character shape of the output unit 21 is formed (Step S12). An outer edge portion E1 having a shape corresponding to the outer surface of the output unit 21, and an inner edge portion E2 having a shape corresponding to the slit 23 and an inner surface of the output unit 21 are formed in an edge of the hole H. A site surrounded by the inner edge portion E2 of the tissue serves as a protrusion P that enters a space formed by ablation. The output unit 21 rather easily comes into contact with and cauterizes tissue because the side opposite to the side where the slit 23 is provided is located on the upper edge portion side of the fossa ovalis O. After the output unit 21 penetrates through the fossa ovalis O and reaches the left atrium L, the supply of the high frequency current to the output unit 21 is stopped. Note that, in a case where the cross-sectional shape of the output unit relative to the central axis of the dilator 40 is a ring shape, when a tissue is cauterized by the output unit, a site of the tissue surrounded by the output unit is cut out in a cylinder shape, and falls off from the fossa ovalis O. However, the output unit 21 in the present embodiment is provided within a range less than 360 degrees, so that the protrusion P does not fall off from the tissue of the fossa ovalis O. Therefore, debris to be carried away by the blood flow is not generated, which results in the relatively high safety of the method. In this process, the protrusion P comes into contact with the tapered tip portion 42, and is turned over in a direction to be pushed down by the dilator 40. Simultaneously, the outer edge portion E1 having a shape corresponding to the outer surface of the output unit 21 comes into contact with the tapered tip portion 42, widens in the radial direction of the hole, and thus can widen the hole. Accordingly, the area of the hole becomes relatively large by the tapered tip portion 42, but the area of the protrusion P does not become too large. Therefore, the ratio of the area of the hole in a state where the ablation is progressed and the hole is widened by the tapered tip portion 42 relative to the area of the protrusion P is larger than the ratio of the area of the hole in a state where the hole is not entirely formed immediately after the ablation is started relative to the area of the protrusion P.

Figure 8A:
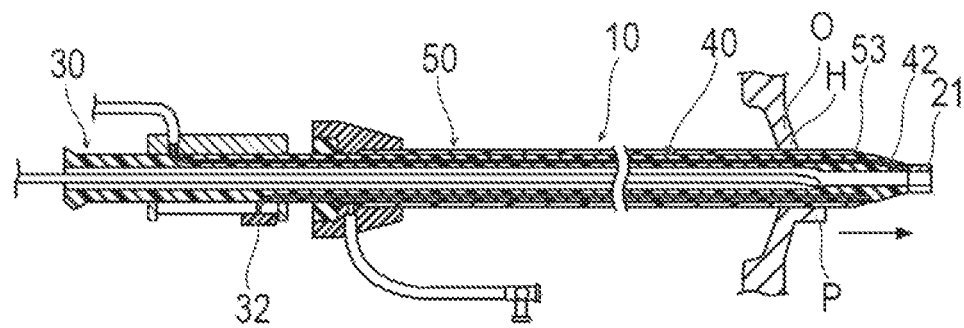

Next, when the medical device 10 is pushed down, as illustrated in FIG. 8A, the tip portion 42 of the dilator 40 and the sheath tapered portion 53 of the outer sheath 50 pass through the fossa ovalis O while expanding the hole H in the fossa ovalis O, and reaches the left atrium L (Step S13). The tip portion 42 and the sheath tapered portion 53 having diameters reduced toward the distal side allow the hole H in the fossa ovalis O to be smoothly widened. In this process, the protrusion P of the tissue being flexible is pushed to the distal side by the tip portion 42, and deforms to the side of the left atrium L. Therefore, the protrusion P does not prevent the dilator 40 from be inserted into the hole H in the fossa ovalis O. Accordingly, the hole H in the fossa ovalis O, even if having the protrusion P, can widen in accordance with the diameter of the outer edge portion E1 (see FIG. 7).

Figure 8B:
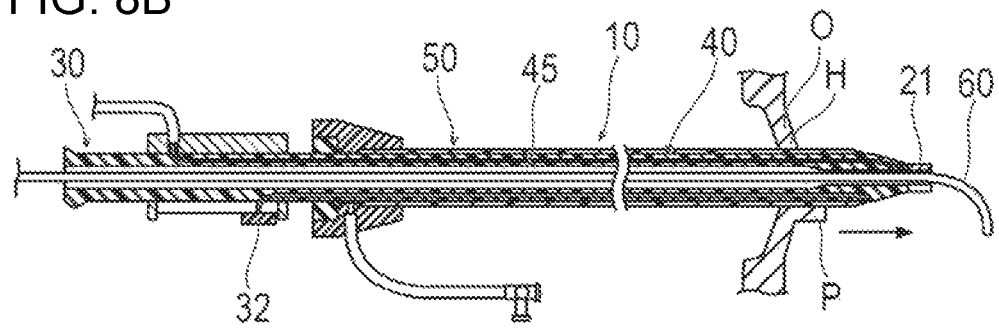

Next, as illustrated in FIG. 8B, the guide wire 60 that is located in the lumen 45 of the dilator 40 is moved to the distal side and allowed to protrude from the dilator 40. With this, a distal portion of the guide wire 60 reaches the left atrium L. Note that, the guide wire 60 may protrude from the dilator 40 and reach the left atrium L, after the hole H is formed in the fossa ovalis O by the output unit 21 and before the dilator 40 is pushed down into the hole H.

Figure 8C:
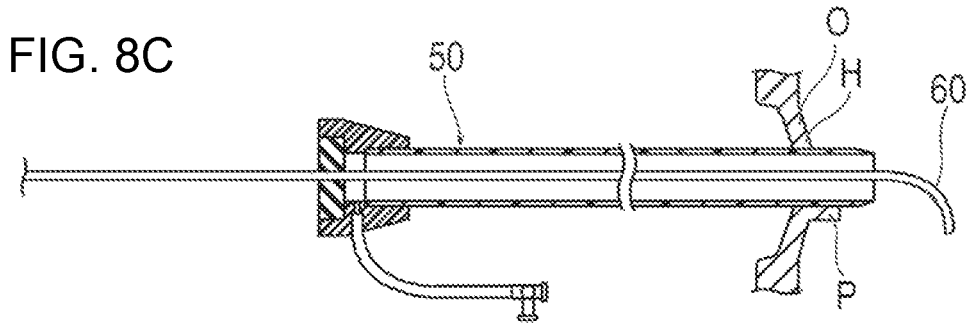

Next, as illustrated in FIG. 8C, the outer sheath 50 and the guide wire 60 are left in the body, and the dilator 40 is extracted to the outside of the body (Step S14). The hole H in the fossa ovalis O widened by the dilator 40 is kept (or maintained) by the outer sheath 50. When the dilator 40 is extracted from the outer sheath 50, the valve body 55 is closed, so that the leakage of the blood and mixing of the air and the like into the blood vessel can be suppressed.

Thereafter, the guide wire 60 is inserted into a target site, and a second medical device such as the outer sheath 50 or an ablation device is inserted along the guide wire 60 (Step S15). In accordance with an exemplary embodiment, the guide wire 60 may be extracted before the second medical device is inserted to the outside of the body, and the second medical device may be inserted without causing the second medical device to be along the guide wire 60. After the ablation in the target site is completed (Step S16), the second medical device is extracted from the outer sheath 50 to the outside of the body (Step S17). In addition, when the outer sheath 50 is extracted, the hole H in the fossa ovalis O is contracted. In this process, as illustrated in FIG. 7, the protrusion P is returned to the hole H in the fossa ovalis O.

Therefore, compared with a case where no protrusion P is formed, a space inside the hole H in which the tissue is destroyed becomes smaller, and the reproduction of the tissue is faster. Note that, the second medical device to be inserted into the living body through the outer sheath 50 is not limited to the ablation catheter. The position (target site) at which the second medical device is inserted through the outer sheath 50 is not limited to the lung vein or the left atrium L, for example, the target site may be the right atrium R, a left atrial appendage, a mitral valve, or the like.

As in the forgoing, the medical device 10 according to the embodiment is the medical device 10 for forming the hole H in the fossa ovalis O (tissue) in a living body and expanding the hole H, the medical device 10 including the dilator 40 (elongated body) inside which the first lumen 45 is formed, the dilator 40 being provided with the tip portion 42 in which the first lumen 45 opens on the distal side, and the output unit 21 that outputs energy for denaturing a tissue of the fossa ovalis O and forming the hole H, in which the output unit 21 is disposed on the tip portion 42 and formed discontinuously in the circumferential direction of the tip portion 42, and the outer diameter of at least one of the tip portion 42 and the output unit 21 gradually decreases toward the distal side.

In the medical device 10 configured as the above, the output unit 21 discontinuous in the circumferential direction of the tip portion 42 is provided to hollow out the tissue and prevent the tissue from falling off, so that it is possible to retain the safety and form the hole H using the energy. In addition, the tip portion 42 the outer diameter of which decreases toward the distal side is provided, so that it is possible to rather easily and smoothly expand the hole H by causing the tip portion 42 to be pushed down into the formed hole H and to pass through the fossa ovalis O. Further, the output unit 21 is not stored in the first lumen 45 of the dilator 40, so that it is not necessary to insert the output unit 21 into a living body from the first lumen 45, and pull out the output unit 21 to the outside of the living body in order to make the interior space in the first lumen 45. Therefore, it is not necessary to replace the guide wire 60 with the output unit 21, and it is possible to insert the guide wire 60 into the hole H in the fossa ovalis through the first lumen 45 that opens in the tip portion 42. Therefore, it is possible to rather easily and rapidly secure the hole H into which a treatment device is inserted, and enhance the working efficiency.

In accordance with an exemplary embodiment, the output unit 21 is located on a distal side of the tip portion 42. With this, pushing down the medical device 10 allows the tip portion 42 that is pushed down subsequent to the output unit 21 to smoothly widen the hole H in the fossa ovalis O formed by the output unit 21.

In addition, the longest distance of the output unit 21 from the central axis in a cross-section vertical to the central axis of the dilator 40 (elongated body) is smaller than the maximum radius of the tip portion 42. In other words, the maximum outer diameter of the output unit 21 is smaller than the maximum outer diameter of the tip portion 42, which helps enable the tip portion having a diameter larger than that of the output unit 21 to effectively widen the hole H in the fossa ovalis O formed by the output unit 21.

In addition, the output unit 21 has a concave shape that surrounds the central axis of the first lumen 45 as viewed from the distal side. In other words, the output unit 21 includes the inner peripheral surface of a concave shape that is recessed as a whole, but of no convex shape or no plane shape. In accordance with an exemplary embodiment, even if the convex shape or the plane shape is partially present in the inner peripheral surface of the output unit, the output unit only needs to have a concave shape as a whole as viewed from the distal side. With this, the protrusion P that protrudes into the space inside the hole H is formed in an edge portion of the hole H in the fossa ovalis O, with the site of a concave shape in the output unit. The protrusion P does not fall off from the tissue in the surrounding and easily deforms, so that it is possible to largely expand the hole H of the tissue.

Moreover, the output unit 21 is provided in a range of 1 degree or more and less than 360 degrees in a direction that surrounds the central axis of the first lumen 45. With this, the large protrusion P that protrudes into the space inside the hole H is formed in the edge portion of the hole H of the tissue, by the output unit 21 that surrounds the central axis of the first lumen 45. The protrusion P does not fall off from the tissue in the surrounding and easily deforms, so that it is possible to largely expand the hole H in the fossa ovalis O.

An angle at which the output unit 21 surrounds the central axis of the first lumen 45 can be, for example, 1 degree or more, preferably 45 degrees or more, more preferably 90 degrees or more, still more preferably 135 degrees or more, still more preferably 180 degrees or more, still more preferably 225 degrees or more, still more preferably 270 degrees or more, and still more preferably 315 degrees or more. When the angle at which the output unit 21 surrounds the central axis of the first lumen 45 is large, the large protrusion P that protrudes into the space inside the hole H is formed in the edge portion of the hole H of the tissue. The large protrusion P easily deforms, so that it is possible to largely expand the hole H of the tissue. Moreover, the angle at which the output unit 21 surrounds the central axis of the first lumen 45 is less than 360 degrees, preferably less than 315 degrees, more preferably less than 270 degrees, still more preferably less than 270 degrees, still more preferably less than 225 degrees, still more preferably less than 180 degrees, still more preferably 135 degrees or more, still more preferably less than 90 degrees, and still more preferably less than 45 degrees. When the angle at which the output unit 21 surrounds the central axis of the first lumen 45 is too large, such a possibility occurs that the protrusion P may fall off from the tissue in the surrounding.

In accordance with an exemplary embodiment, the output unit 21 is a pipe body that is discontinuous in the circumferential direction and has the slit 23 (notch). With this, the large protrusion P that protrudes into the space inside the hole H is formed in the edge portion of the hole H of the tissue. Note that, the cross-sectional shape of the discontinuous pipe body is not limited to a perfect circle, but may be an ellipse, a quadrangle, or a triangle, for example.

In addition, the output unit 21 is located at a distal-side end face of the dilator 40 (elongated body) and includes the slit 23 (notch) that extends in the axial direction, and the distal-side end face of the dilator 40 is continuous in a ring shape, which helps enable the protrusion P formed by the output unit 21 to be pushed down by the dilator 40 continuous in a ring shape to largely widen the hole H. In accordance with an exemplary embodiment, the end face of the dilator 40 is continuous in a ring shape, so that it is possible to prevent the protrusion P from entering the first lumen 45 of the dilator 40, and suppress the protrusion P from interfering with a device that passes through the first lumen 45.

Figure 10:
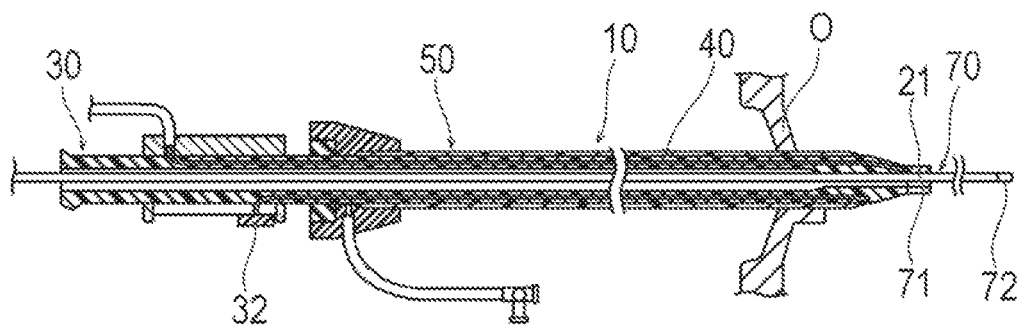
FIG. 10 is a cross-sectional view illustrating another usage method of the medical device.

In accordance with an exemplary embodiment, the dilator 40 includes the dilator bend 48 (bend) that bends in one direction toward the distal side, and the direction in which the output unit 21 is located with respect to the central axis of the dilator 40 is opposite to the direction in which the dilator bend 48 bends toward the distal side. In other words, the direction in which the slit 23 is located with respect to the central axis of the dilator 40 is the same as the direction in which the dilator bend 48 bends toward the distal side. With this, when the dilator 40 is pushed down into the fossa ovalis O, the output unit 21 is located in the direction in which the dilator 40 is pushed down. Therefore, it is possible to effectively cauterize the tissue. In addition, as illustrated in FIG. 10, when an ablation device 70 is inserted into the first lumen 45, the ablation device 70 easily comes into contact with the output unit 21. Therefore, for example, energy (current) can be supplied from the output unit 21 to the ablation device 70. The ablation device 70 includes a power receiving unit 71 that is electrically connected to an ablation electrode 72 at a tip of the ablation device 70, in the site where the output unit 21 comes into contact with the ablation device 70. The ablation device 70 can receive the current from the power receiving unit 71, and can perform the ablation with the electrode 72. Note that, the direction in which the output unit 21 is located with respect to the central axis of the dilator 40 may be the same as the direction in which the dilator bend 48 bends toward the distal side. In this case, the guide wire 60 and the ablation device 70 that pass through the first lumen 45 hardly comes into contact with the output unit 21, so that it is possible to suppress an interference between the output unit 21 and the other members.

In accordance with an exemplary embodiment, the medical device 10 includes the operation wire 35 that extends along the axial direction of the dilator 40, and a distal portion of the operation wire 35 is interlocked with the distal portion of the dilator 40 or the distal portion of the energy output unit 20. With this, the dilator 40 can be bent by pulling the operation wire 35. Therefore, it is possible to relatively easily adjust a position in which the hole H in the fossa ovalis O is formed.

In addition, the present disclosure includes a treatment method (therapeutic method) of forming, by using the abovementioned the medical device 10, the hole H in the fossa ovalis O (tissue) in a living body, and expanding the hole H. The treatment method includes: Step S10 of inserting a distal portion of the medical device 10 into the living body; Step S12 of forming, by bringing the output unit 21 into contact with the fossa ovalis O, the hole H in the fossa ovalis O; and Step S13 of widening, by moving the dilator 40 to the distal side, the hole H in the fossa ovalis O by at least one of the tip portion 42 and the output unit 21.

The treatment method configured as the above forms the hole H by the output unit 21 that is provided in the range of less than 360 degrees in the direction that the surrounds the central axis of the first lumen 45 that opens in the tip portion 42 to hollow out the tissue and prevent the tissue from falling off, so that it is possible to retain the safety and form the hole H using the energy. In addition, the tip portion 42 is pushed down into the formed hole H to widen the fossa ovalis O, so that it is possible to rather easily and smoothly expand the hole H. Further, the output unit 21 is not stored in the first lumen 45 of the dilator 40, so that it is possible to insert the guide wire 60 into the hole H in the fossa ovalis through the first lumen 45 that opens in the tip portion 42, without pulling out the output unit 21 to the outside of the living body. Therefore, it is possible to rather easily and rapidly secure the hole H into which a treatment device is inserted, and enhance the working efficiency.

Note that, the present disclosure is not limited to the above-described embodiment, but various changes by those skilled in the art can be made within the technical scope of the present invention. For example, the tissue in which a hole is created by the medical device 10 need not to be the fossa ovalis O.

Figure 11A:
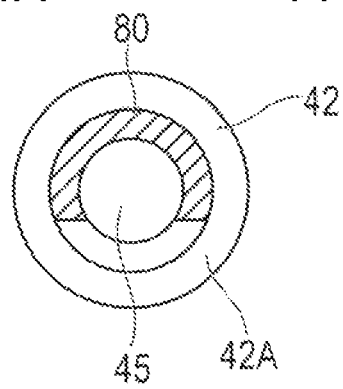
Figure 11B:
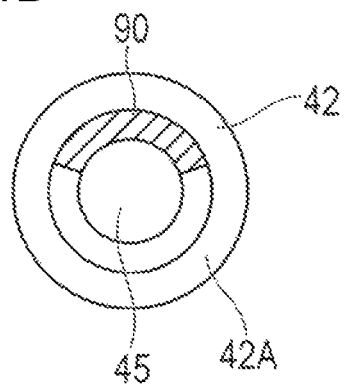

In addition, as a first denaturation example illustrated in FIG. 11A, an output unit 80 serving as an electrode may be provided in a part in the circumferential direction so as to be cut with a plane in parallel with the central axis of the first lumen 45. Note that, same reference numerals are assigned to parts having the similar functions as those in the aforementioned embodiment, and explanations of the same reference numbers and functions are omitted. In accordance with an exemplary embodiment, as a second denaturation example illustrated in FIG. 11B, an output unit 90 may be provided in a range of less than 180 degrees in a direction that surrounds the central axis of the first lumen 45.

Figure 12A:
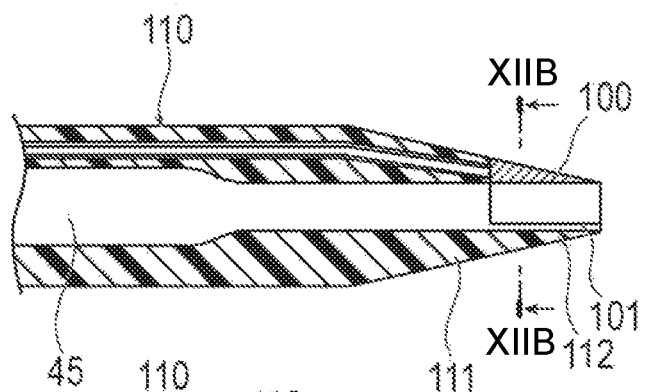
Figure 12B:
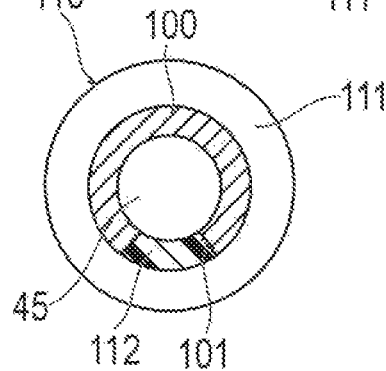
Figure 13A:
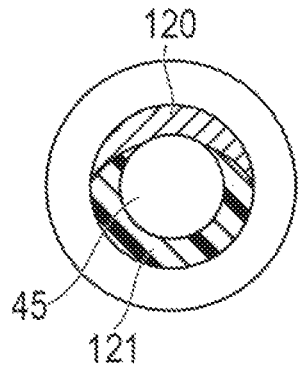
Figure 13B:
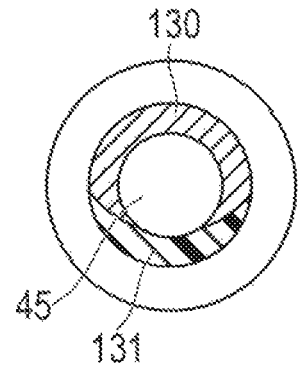

In accordance with an exemplary embodiment, as a third denaturation example illustrated in FIGS. 12A and 12B, an output unit 100 may have a tapered outer diameter that is reduced toward the distal side. The output unit 100 is smoothly continuous with a tapered tip portion 111 of a dilator 110. In a discontinuous site in the circumferential direction of the output unit 100, a supplementation part 112 that constitutes the tip portion 111 of the dilator 110 is provided so as to be smoothly continuous with an outer peripheral surface of the output unit 100, which allows the output unit 100 and the tip portion 111 to smoothly widen a hole to be formed in a tissue. A plane 101 to be interlocked with the supplementation part 112 of the output unit 100 may include a plurality of asperities in order to increase the joining force. In accordance with an exemplary embodiment, no supplementation part 112 may be provided. Moreover, as a fourth denaturation example illustrated in FIG. 13A, an output unit 120 may be formed in a crescent shape, in a cross-sectional shape vertical to the central axis of the first lumen 45. In a joint portion between the output unit 120 and a supplementation part 121, the output unit 120 is located outside in the radial direction of the supplementation part 121. Moreover, as a fifth denaturation example illustrated in FIG. 13B, a supplementation part 131 that becomes discontinuous in a circumferential direction of an output unit 130 may be formed in a crescent shape. In a joint portion between the output unit 130 and the supplementation part 131, the supplementation part 131 is located outside in the radial direction of the output unit 130.

Figure 14A:
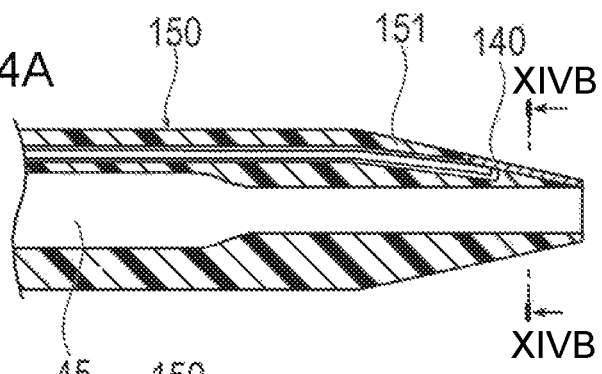
Figure 14B:
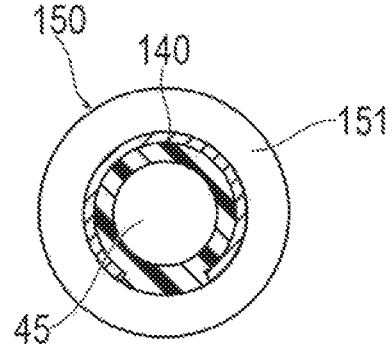

In accordance with an exemplary embodiment, as a sixth denaturation example illustrated in FIGS. 14A and 14B, an output unit 140 may be disposed so as to cover a distal-side portion of a tip portion 151 of a dilator 150. Outer peripheral surfaces of the tip portion 151 and the output unit 140 are smoothly continuous with each other, which allow the output unit 140 and the tip portion 151 to smoothly widen a hole to be formed in a tissue.

Figure 15A:
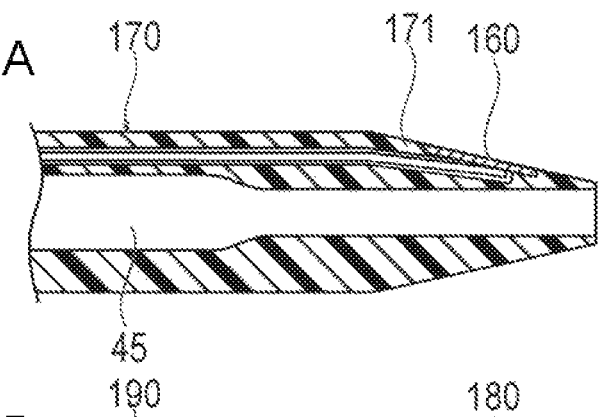

In accordance with an exemplary embodiment, as a seventh denaturation example illustrated in FIG. 15A, an output unit 160 may be provided on a proximal side from the most distal portion of a tip portion 171 of a dilator 170. Even with such a configuration, the dilator 170 is abutted against a tissue to cause the tip portion 171 to be cut into the tissue, so that the output unit 160 can come into contact with the tissue. Accordingly, even with such a configuration, a hole is made in the tissue by the output unit 160, and the dilator 170 can be pushed down into the hole.

Figure 15B:
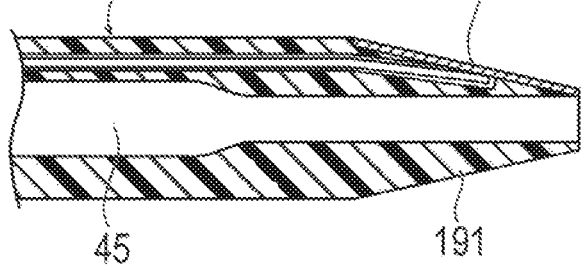

In accordance with an exemplary embodiment, as an eighth denaturation example illustrated in FIG. 15B, an output unit 180 may be provided across a tip portion 191 of a dilator 190 from a distal side of the tip portion 191 to a proximal side of the tip portion 191.

Figure 16:
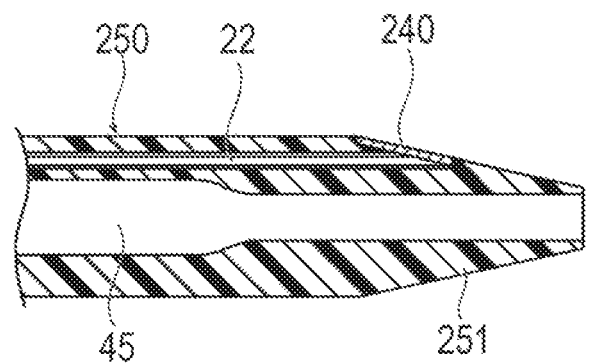
FIG. 16 is a cross-sectional view illustrating a ninth denaturation example of the medical device.

In accordance with an exemplary embodiment, as a ninth denaturation example illustrated in FIG. 16, an output unit 240 may be provided not on a distal-side portion of a tip portion 251 of a dilator 250 but on a proximal-side portion of the tip portion 251 on the proximal side. With this, it is possible to form a hole having the large outer edge portion E1 by the output unit 240, while decreasing a range in which a tissue is destroyed by the output unit 240.

Figure 17:
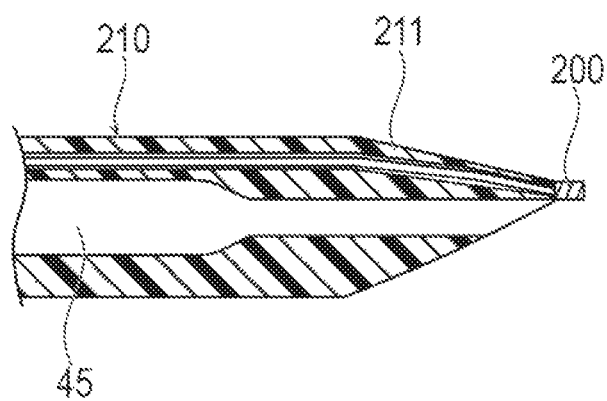
FIG. 17 is a cross-sectional view illustrating a tenth denaturation example of the medical device.
Figure 18:
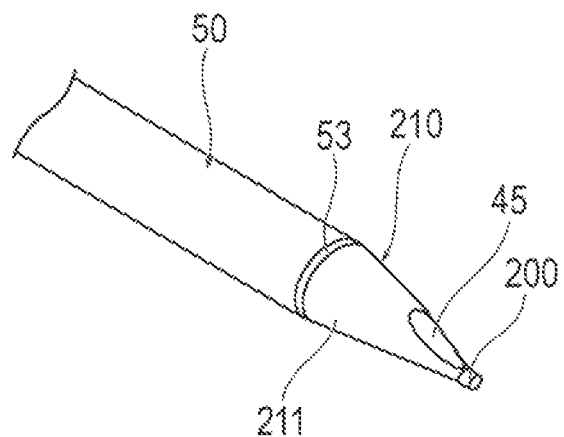
FIG. 18 is a perspective view illustrating the tenth denaturation example of the medical device.

In accordance with an exemplary embodiment, as a tenth denaturation example illustrated in FIGS. 17 and 18, an output unit 200 need not to have a concave shape on a side toward the central axis of the first lumen 45 as viewed from the distal side. The output unit 200 has a cylinder shape, for example. Even with such a configuration, the output unit 200 is formed discontinuously in the circumferential direction of a tip portion 211. Therefore, after a hole is formed in a tissue by the output unit 200, the tip portion 211 of a dilator 210 in which the first lumen 45 is opened can be inserted into the hole. The first lumen 45 may open in an inclined surface of the tip portion 211. Accordingly, the opening of the first lumen 45 is inclined with respect to a plane vertical to the central axis of the first lumen 45. With this, when the tip portion 211 is inserted into the hole in the tissue, an edge portion of the opening of the first lumen 45 is difficult to become a resistance, so that it is possible to smoothly widen the hole. Note that, the opening of the first lumen 45 may be formed in a plane vertical to the central axis of the first lumen 45.

Figure 19:
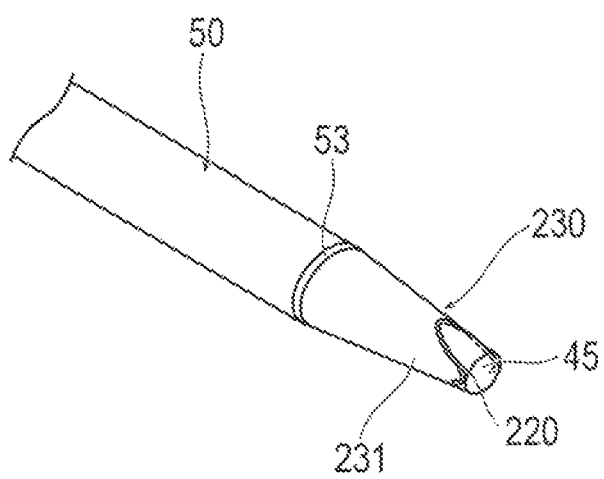
FIG. 19 is a perspective view illustrating an eleventh denaturation example of the medical device.

In accordance with an exemplary embodiment, as an eleventh denaturation example illustrated in FIG. 19, the output unit 200 may have a wire shape, not a plate shape. The output unit 200 is provided an outer surface of a tip portion 221 of a dilator 220. The shape of the output unit 200 is not specially limited, and for example, both ends are located in the vicinity of the opening of the first lumen 45, and a center of the output unit 200 is curved toward the proximal side.

In accordance with an exemplary embodiment, the output unit may be a bipolar electrode having two electrodes. In this case, a counter electrode plate to be paired up with the output unit is provided in any portion of the tip portion that comes into contact with the tissue. The electrode area where the counter electrode plate appears is larger than the area of the output unit.

The detailed description above describes to a medical device and a treatment method for forming a hole in a tissue. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A transseptal dilator for forming a hole in a fossa ovalis in a living body and expanding the hole, the transseptal dilator comprising:
 an elongated body having at least one lumen formed inside of the elongated body, the elongated body including a tip portion in which the at least one lumen opens on a distal side, the at least one lumen of the elongated body including a first lumen configured to receive a guide wire, and the elongated body including a bend portion configured to bend at a prescribed angle in a state where no external forces from an outer sheath are acting on the bend portion, the prescribed angle being 10 degrees to 90 degrees;

an output unit configured to output energy for denaturing the fossa ovalis and forming the hole, the output unit being a cylindrical tubular body extending in an axial direction and disposed on a distal end of the tip portion of the elongated body and formed discontinuously in a circumferential direction of the tip portion with a slit extending from a proximal end of the output unit to a distal end of the output unit, the slit extending from an outer surface of the output unit to an inner surface of the output unit, and wherein the output unit is an electrode configured to form the hole in the fossa ovalis in the living body without the use of a transseptal needle and having a C-character shape in a cross-section vertical to a central axis of the elongated body;

the tip portion including an outer diameter decreasing toward a distal side of the transseptal dilator; and wherein the prescribed angle of 10 degrees to 90 degrees of the bend portion is between an extension of an axis of a proximal portion of the elongated body in a distal direction and an axis substantially parallel to the cylindrical tubular body of the output unit.

2. The transseptal dilator according to claim 1, wherein a distance from a central axis of the output unit in a cross-section vertical to the central axis of the elongated body is smaller than a maximum radius of the tip portion.

3. The transseptal dilator according to claim 1, wherein the output unit has a concave shape that surrounds a central axis of a lumen of the output unit as viewed from the distal end of the tip portion.

4. The transseptal dilator according to claim 1, wherein the output unit is located at a distal-side end face of the elongated body and the distal-side end face of the elongated body is continuous in a ring shape.

5. The transseptal dilator according to claim 1, further comprising:

a conductive wire configured to be connected to the electrode to output unit and to conduct a current to the electrode of the output unit.

6. The transseptal dilator according to claim 1, wherein the at least one lumen of the elongated body further comprises:

a second lumen configured to receive a conductive wire of the output unit; and a third lumen configured to receive an operation wire for bending the elongated body.

7. The transseptal dilator according to claim 1, wherein the output unit is continuous with the tapered tip portion of the elongated body; and a supplementation part that constitutes the tip portion of the elongated body and is continuous with an outer peripheral surface of the output unit.

8. The transseptal dilator according to claim 1, wherein the output unit is configured to be disposed to cover a distal-side portion of the tip portion of the elongated body, and wherein outer peripheral surfaces of the tip portion and the output unit are continuous with each other.

9. The transseptal dilator according to claim 1, wherein the outer diameter of an outer peripheral surface of the output unit is smaller than a maximum outer diameter of the tip portion;

an inner diameter of an inner peripheral surface of the output unit is equivalent to an inner diameter of a distal side lumen of the first lumen, the first lumen configured to receive the guide wire and wherein the first lumen includes the distal side lumen on a distal side, a proximal side lumen having a lumen larger than the inner diameter of the distal side lumen, and central lumen having an inner diameter that changes between the distal side lumen and the proximal side lumen; and wherein the output unit has a length in the axial direction of 0.1 mm to 5.0 mm.

10. The transseptal dilator according to claim 1, further comprising:

the outer sheath, the outer sheath configured to receive the elongated body and having an inner peripheral surface configured to allow the elongated body to slide within a sheath main body of the outer sheath, and wherein the sheath main body includes a sheath bend in a distal portion of the sheath main body that bends at a prescribed angle in a natural state, the prescribed angle of the sheath bend relative to a proximal portion of the sheath main body being 0 degrees to 90 degrees.

11. The transseptal dilator according to claim 10, wherein the sheath main body include a tapered portion have a diameter of which is reduced toward a distal side end portion of the sheath main body, and wherein an inclined angle relative to a central axis of the tapered portion is 1 degree to 15 degrees; and the prescribed angle of the bend portion of the elongated body is 40 degrees to 70 degrees.

12. A transseptal dilator for forming a hole in a fossa ovalis in a living body and expanding the hole, the transseptal dilator comprising:

an elongated body having a first lumen and a second lumen formed inside of the elongated body, the elongated body including a tip portion in which the first lumen opens on a distal side, the first lumen configured to receive a guide wire and the elongated body including a bend portion configured to bend at a prescribed angle in a state where no external forces from an outer sheath are acting on the bend portion, the prescribed angle being 10 degrees to 90 degrees;

an output unit configured to output energy for denaturing the fossa ovalis and forming the hole without using a transseptal needle;

a conductive wire received in the second lumen and connected to the output unit;

the tip portion including an outer diameter decreasing toward a distal side of the transseptal dilator;

the output unit is configured to be disposed on the distal end surface of the tip portion in a range of less than 360 degrees; and wherein the prescribed angle of 10 degrees to 90 degrees of the bend portion is between an extension of an axis of a proximal portion the elongated body in a distal direction and an axis substantially parallel to the tip portion of the elongated body.

13. The transseptal dilator according to claim 12, wherein an outer diameter of the output unit decreases toward the distal side of the transseptal dilator and an angle of the decrease of the outer diameter of the output unit is same as an angle of the decrease of the outer diameter of the tip portion.

14. The transseptal dilator according to claim 12, wherein the first lumen in a cross-section vertical to a central axis of the elongated body having a circular cross-section from a proximal end to a distal end of the first lumen; and wherein a central axis of the second lumen is other than coaxial with a central axis of the first lumen.

15. The transseptal dilator according to claim 12, further comprising:

a distal end of the conductive wire is located on a distal end surface of the tip portion.

16. The transseptal dilator according to claim 12, further comprising:
a distal end of the conductive wire is located proximal to a distal end surface of the tip portion.

17. A transseptal dilator for forming a hole in a fossa ovalis in a living body and expanding the hole, the transseptal dilator comprising:
an elongated body having a lumen formed inside of the elongated body, the elongated body including a bend portion in a distal portion of the elongated body and a tip portion distal of the bend portion in which the lumen opens on a distal side of elongated body, the lumen configured to receive a guide wire and the bend portion of the elongated body being configured to bend at a prescribed angle in a state where no external forces from an outer sheath are acting on the bend portion, the prescribed angle being 10 degrees to 90 degrees;
an output unit configured to output energy for denaturing the fossa ovalis and forming the hole without the use of a transseptal needle, the output unit being disposed on the tip portion of the elongated body and formed discontinuously in a circumferential direction of the tip portion, the output unit is located on the tip portion in a range of less than 360 degrees;
wherein, a direction that the output unit is located with respect to a central axis of the elongated body is opposite to a direction that the bend portion bends toward the distal side; and
wherein the prescribed angle of 10 degrees to 90 degrees of the bend portion is between an extension of an axis of a proximal portion of the elongated body in a distal direction and an axis substantially parallel to the tip portion of the elongated body.

18. The transseptal dilator according to claim 17, wherein an angle that the output unit surrounds the central axis of the elongated body is 1 degree to 270 degrees, and wherein a distal end of the output unit is an electrode configured to form the hole in the fossa ovalis of the living body, and the prescribed angle of the bend portion is 40 degrees to 70 degrees.

19. The transseptal dilator according to claim 17, wherein an angle that the output unit surrounds the central axis of the elongated body is 45 degrees to 180 degrees, and wherein a distal end of the output unit is an electrode configured to form the hole in the fossa ovalis of the living body.

20. A transseptal dilator for forming a hole in a fossa ovalis in a living body and expanding the hole, the transseptal dilator comprising:
an elongated body having a lumen formed inside of the elongated body, the elongated body including a tip portion in which the lumen opens on a distal side, the lumen configured to receive a guide wire and the elongated body including a bend portion configured to bend at a prescribed angle in a state where no external forces from an outer sheath are acting on the bend portion, the prescribed angle being 10 degrees to 90 degrees;
an output unit configured to output energy for denaturing the fossa ovalis and forming the hole without use of a transseptal needle;
an entire circumference of the tip portion uniformly decreasing toward a distal side of the transseptal dilator;
the output unit being located on an outer surface of the tip portion in a range of less than 360 degrees, and wherein an outer diameter of the output unit decreases toward the distal side of the transseptal dilator and an angle of decrease of the outer diameter of the output unit is same as an angle of decrease of the entire circumference of the tip portion; and
wherein the prescribed angle of 10 degrees to 90 degrees of the bend portion is between an extension of an axis of a proximal portion of the elongated body in a distal direction and an axis substantially parallel to the tip portion of the elongated body.

* * * * *